(12) United States Patent
Hanson

(10) Patent No.: US 6,506,049 B2
(45) Date of Patent: Jan. 14, 2003

(54) ORTHODONTIC BRACKETS AND CONVERTIBLE BUCCAL TUBES

(75) Inventor: G. Herbert Hanson, Hamilton (CA)

(73) Assignee: Augusta Developments Inc., Hamilton (CA)

( * ) Notice: Subject to any disclaimer, the term of this patent is extended or adjusted under 35 U.S.C. 154(b) by 0 days.

(21) Appl. No.: 09/796,506

(22) Filed: Mar. 2, 2001

(65) Prior Publication Data

US 2002/0034715 A1 Mar. 21, 2002

Related U.S. Application Data

(63) Continuation-in-part of application No. 09/666,036, filed on Sep. 20, 2000, now abandoned.

(51) Int. Cl.⁷ .................................................. A61C 7/00
(52) U.S. Cl. .......................................... 433/11; 433/17
(58) Field of Search ................................ 433/10, 11, 13, 433/14, 17

(56) References Cited

U.S. PATENT DOCUMENTS

| | | | | |
|---|---|---|---|---|
| 3,091,857 A | * | 6/1963 | Rubin et al. | 433/11 |
| 4,443,189 A | * | 4/1984 | Wildman | 433/10 |
| 4,712,999 A | * | 12/1987 | Rosenberg | 433/11 |
| 5,908,293 A | * | 6/1999 | Vourdouris | 433/10 |

* cited by examiner

Primary Examiner—Cary E. O'Connor

(74) Attorney, Agent, or Firm—Stanley J. Rogers

(57) ABSTRACT

A new structure is provided for orthodontic devices comprising a bracket or a convertible buccal tube, both of which have a body with a mesial-distal extending arch wire receiving slot therein. Both have a slot closure member, also referred to as a jamming shutter, pivotally mounted by the body for movement between slot open and closed positions and consisting of a pivot portion including an arm portion with a mesially-distally extending slot closure portion at its end. The slot closure portion has a part that closes the slot and mesially-distally extending parts that in the slot closed position engage an adjacent body surface with an interference jamming fit sufficient to retain the slot closure member in slot closed position. Any movement of the slot closure member to and from the slot closed position involves flexing of these engaged parts away from the device body against the elasticity of the material, removing the need for latches or retaining springs. The body or the closure member has a recess into which an opening tool can be inserted and rotated to open the closure member. A bracket will usually be "active", including a flat attitude controlling spring having a free end protruding into the slot to engage with an arch wire therein. A surface of the pivot portion can be a cam that in slot open position holds the spring out of the slot, so that the wire can be more easily inserted and removed. In brackets for incisors or canines the bracket body labial-lingual dimension decreases progressively from the lingual to the labial; with the slot closed the occlusal surface is unobstructed and forms a bite plane engaged by the cutting edge of the opposed tooth during biting action to oppose overbite. A convertible buccal tube employs the same basic structure and has the slot opening at an appropriate surface with the slot closure member, and an attitude controlling spring if provided, similarly mounted in the body.

35 Claims, 6 Drawing Sheets

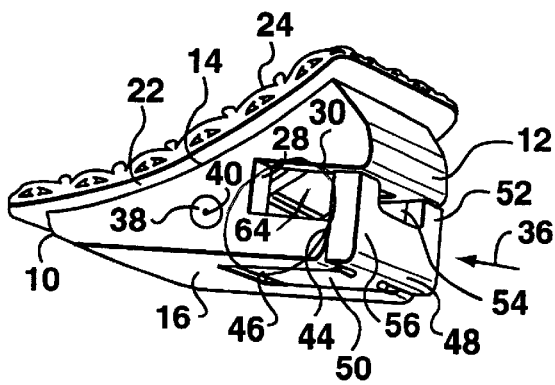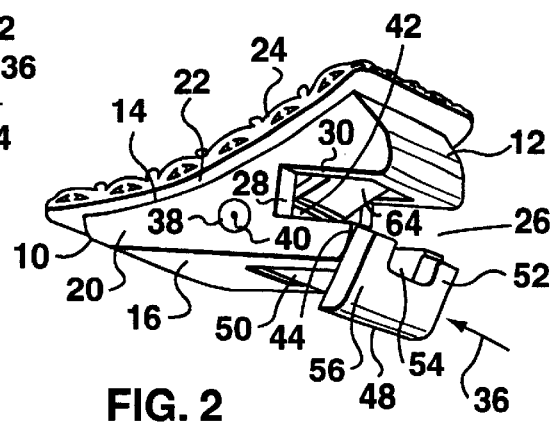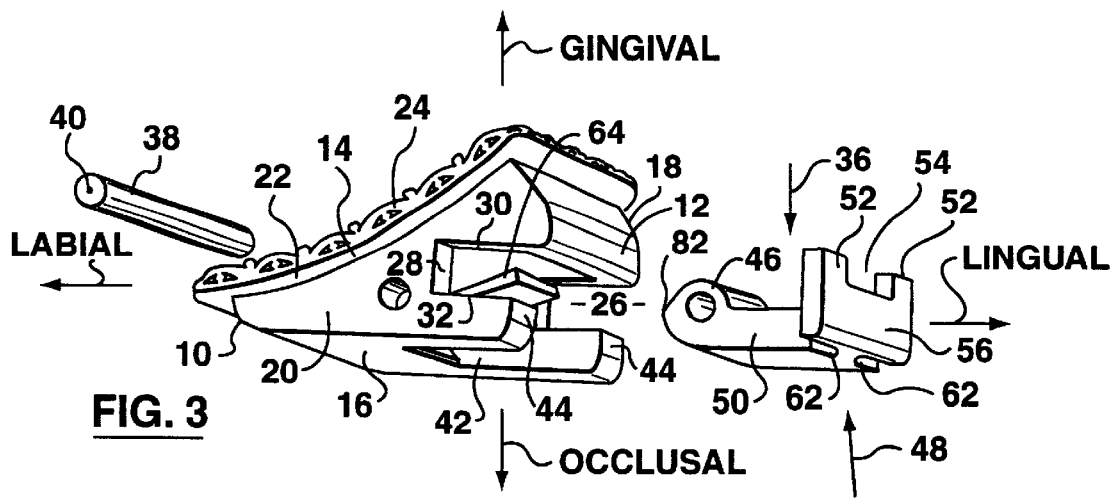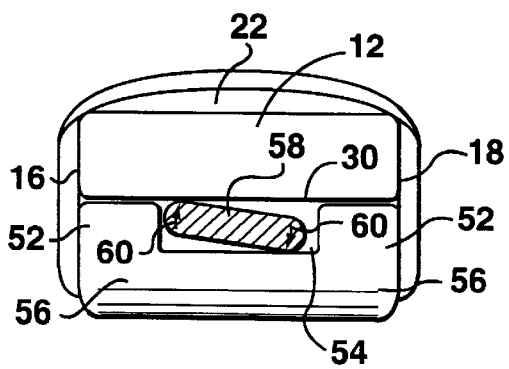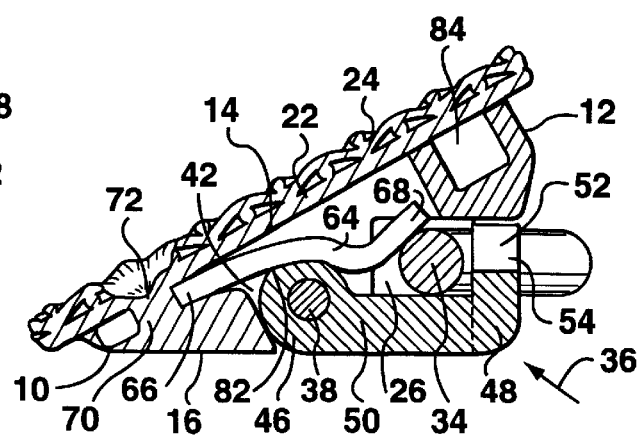

ORTHODONTIC BRACKETS AND CONVERTIBLE BUCCAL TUBES

CROSS REFERENCE TO A RELATED APPLICATION

This application is a continuation in part of my application Ser. No. 09/666,036, filed Sep. 20, 2000, now abandoned.

FIELD OF THE INVENTION

This invention is concerned with improvements in or relating to orthodontic devices consisting of orthodontic brackets, particularly orthodontic brackets which comprise arch wire attitude controlling spring means as a permanent part thereof, and buccal tubes of convertible type, which may also comprise arch wire attitude controlling spring means as a permanent part thereof.

REVEIW OF PRIOR ART

Orthodontic procedures almost always employ a plurality of orthodontic brackets that are attached to respective teeth, increasingly by cementing them to the teeth, although in some circumstances the bracket still may be attached to a metal band which embraces the tooth. Each bracket has a mesial distal extending slot therein, usually of rectangular cross section in a gingival occlusal plane, and the brackets are connected together using an arch wire, so called because it is preformed to an optimum arch shape corresponding to the desired conformation of the teeth at the conclusion of the procedure. Arch wires of progressively increasing stiffness and, depending on the type of tooth movement to be achieved, also of different cross sections, are used one at a time, the wire being retained in the slots by ligating means of some kind. Initially the brackets themselves were "passive", in that ligation of the wire to the bracket to obtain the necessary action between them was external to the bracket, at first consisting of a soft metal wire twisted around the bracket, while later an elastomeric hoop or loop increasingly was commonly used in place of the wire. In another line of development each bracket was made to be "active" in that it comprised a permanent ligating spring member. Specific examples of such active brackets are disclosed and claimed in my U.S. Pat. Nos. 3,772,787; 4,248,588; 4,492,573; 4,698,017; 5,685,711; 5,711,666 and 5,906,486, the disclosures of which are incorporated herein by this reference. Brackets of this type currently are used in the Hanson SPEED System (Trade Mark) and have proven to be very successful.

The ends of the arch wire may be engaged in so-called buccal tubes, usually attached to the molars on respective sides of the patient's mouth so as to anchor the arch wire firmly in place, and buccal tubes may also be employed on intermediate teeth in place of brackets whenever this is appropriate. In its simplest form a buccal tube is passive and consists of a short piece of tube attached to a base by which it is mounted on the tooth surface, the tube bore opening at least mesially so that the arch wire end must be inserted therein by moving it distally. This is not always convenient, and may not be possible when the buccal tube is on an intermediate tooth, and the solution is then to use a buccal tube of the so-called convertible type, with which one side of the tube bore can be opened when required for insertion of the wire therein or its removal. It is also possible to incorporate in the tube a wire engaging attitude controlling spring member that will urge the wire into contact with two of the slot walls, whereupon the tube is active as well as convertible.

It will be apparent from the foregoing brief general description of brackets and buccal tubes that there can be considerable overlap between both their function and appearance, with the result that it may be possible for a particular orthodontic device to be considered by some orthodontists as a bracket, while others will think of it as a buccal tube. In general, a device in which its body is noticeably bigger in gingival-occlusal dimension than mesiall-distally will usually be regarded by most practitioners as a bracket, while one in which the opposite is the case will be regarded as a buccal tube.

Inherently buccal tubes, especially those of the passive type, are smaller than most brackets and can have a smooth exterior. There is a constant endeavor to provide brackets that are as small and as smooth exteriorly as possible, for cosmetic reasons to please the patient, in order to reduce as much as possible any rough contact between the tongue, the brackets and the adjacent mouth tissue, with consequent discomfort, and for hygienic reasons to reduce the number of areas in which food and dental plaque can accumulate. The orthodontist is interested in addition to use both brackets and buccal tubes that while low in cost provide fast, precise and effective movement and attitude control of the teeth.

There is also increasing interest in the so-called lingual technique, in which the brackets are mounted on the lingual tooth surfaces, so that they and the arch wire are concealed from frontal view. Lingual procedures are more difficult to implement and a compromise is to use a lingual technique only for the upper arch, where the brackets and arch wire would otherwise be most visible, and a labial technique for the lower arch, where the brackets and arch wire are mostly hidden by the lower lip. Lingual and mixed lingual/labial procedures are of special interest to adult patients who are more concerned than children with appearance during the two to three year period required for a typical procedure. Small smooth brackets are needed particularly for the lingual location because of ready access by the tongue, and the natural tendency for the tongue to explore any foreign object in the mouth. Attempts simply to reduce the size of existing brackets are not generally successful, at least partly because changes in scale affects size parameters in different ratios, e.g. areas decrease in square ratio while volumes decrease in cube ratio, with the result that it becomes increasingly difficult, especially with the tiny spring members required, to find materials of the necessary properties. Examples of such small smooth exterior brackets suitable for lingual procedures are those described and claimed in my U.S. Pat. Nos. 4,698,017 and 5,685,711, issued respectively Oct. 6, 1987 and Nov. 11, 1997, referred to above.

Orthodontics is now a well established branch of dentistry, and the manufacture of orthodontic equipment is a mature industry. The ongoing requirement to provide appliances that are efficient, economical and easy to use increasingly has the added requirement to be as inexpensive as possible, especially if orthodontists are to be persuaded to make the changes in the procedures in which they were trained, and with which they are very familiar, that the adoption of new devices usually entails.

SUMMARY OF THE INVENTION

It is a principal object of the invention therefore to provide new orthodontic brackets, which preferably are of the type comprising a permanent attitude controlling metal spring that can engage an arch wire in the arch wire receiving slot, and buccal tubes of the so-called convertible type, which may also comprise a permanent attitude controlling metal spring.

It is another principal object to provide new brackets of small size and of an exterior shape that makes them specially suitable for use in lingual techniques, particularly in association with incisor or canine teeth.

It is a further object to provide such new brackets and convertible buccal tubes requiring a minimum number of parts and in which the cost of their fabrication is minimized.

In accordance with the invention there is provided an orthodontic device comprising:

a device body having labial, lingual, gingival, occlusal, mesial and distal surface portions, the body having therein a mesial-distal extending arch wire receiving slot having one side open to a device body surface portion to permit insertion of an arch wire into the slot, and a slot closure member mounted by the device body so as to be movable about a pivot axis between a slot open position in which the open slot side is open, and a slot closed position in which the closure member closes the open slot side to retain an orthodontic arch wire in the slot;

wherein the slot closure member comprises:

a pivot portion mounted by the device body for the pivoting movement of the slot closure member about the pivot axis; and a slot closure portion movable with the pivot portion and extending mesially-distally with respect to the device body;

and wherein the slot closure portion comprises:

a slot closure part that in the slot closed position closes the open side of the arch wire slot; and at least one mesially-distally extending body engaging part that in the slot closed position of the slot closure member engages with an immediately adjacent surface portion of the device body with a rubbing, butting interference fit engagement between them providing a retaining force such that the slot closure member is retained thereby in the slot closed position, and such that movement of the slot closure member into the slot closed position requires flexing of the body engaging part in a direction away from the device body against the resilience of the material of the body engaging part.

Devices of the invention may constitute an orthodontic bracket or a convertible buccal tube.

Preferably there is provided in a recess within the device body a flat attitude controlling spring member having a fixed end portion fixed to the device body and a free end portion extending into the arch wire receiving slot for engagement in a mesially-distally extending plane with an arch wire in the slot, such engagement urging the arch wire toward the slot closure part.

Further in accordance with the invention there is provided an orthodontic bracket for application to the lingual surface of an incisor or canine tooth, which teeth are characterized in that their labial-lingual dimension increases progressively from the gingival to the occlusal, the bracket comprising:

a bracket body having labial, lingual, gingival, occlusal, mesial and distal surface portions, having therein a mesial-distal extending arch wire receiving slot with its lingual side open to the lingual surface portion to permit insertion of an arch wire into the slot, and having therein a recess opening to the lingual and occlusal surface portions;

the bracket body also comprising a slot closure member mounted by the bracket body in the recess so as to be movable about a pivot axis between a slot open position in which the open slot side is open, and a slot closed position in which it closes the open slot side to retain an orthodontic arch wire therein, the slot closure member also having labial, lingual, gingival, occlusal, mesial and distal surface portions;

wherein in the slot closed position the occlusal surface portion of the slot closure member is flush with the occlusal surface portion of the bracket body to thereby provide a combined occlusal surface which is unobstructed; and wherein the gingival-occlusal dimension of the bracket body decreases progressively from the lingual to the labial, the decrease corresponding to the average increase from the occlusal to the gingival of an incisor or canine tooth, so that when the bracket is attached to the lingual surface of an incisor or canine tooth the unobstructed combined occlusal surface provides a mesial-distal, labial-lingual extending bite plane surface which the tooth edge at the junction of the occlusal and labial surface portions of an opposed incisor or canine tooth can engage during biting action to oppose overbite.

Description of The Drawings

Particular preferred embodiments of the invention will now be described, by way of example with reference to the accompanying diagrammatic drawings wherein:

FIG. 1 is a perspective view from the mesial-occlusal of a first embodiment with the pivoting slot closure member in slot closed position;

FIG. 2 is a similar perspective view with the slot closure member in slot open position;

FIG. 3 is an exploded view from the same perspective as FIGS. 1 and 2 of the first embodiment;

FIG. 4 is a view in elevation from the lingual of the bracket of FIGS. 1–3 with the slot closure member in slot closed position, showing in cross section the operative end of a flat-ended tool used to move the slot closure member to slot open position;

FIG. 5 is a cross section in a lingual-labial, gingival-occlusal plane through the bracket with the slot closure member in slot closed position, and with an arch wire of round cross section retained in the slot;

DESCRIPTION OF THE PREFERRED EMBODIMENTS

Figure 6:
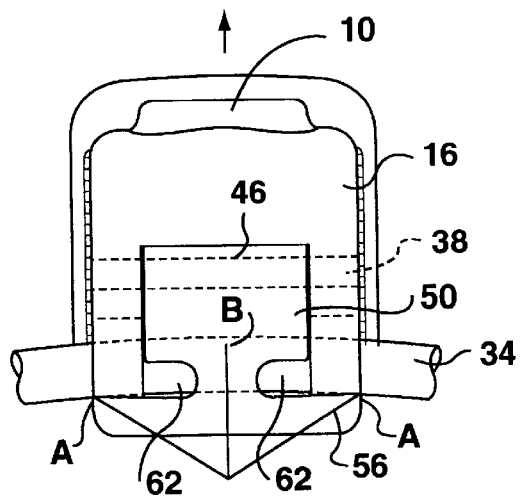
FIG. 6 is a view in elevation from the occlusal of the first embodiment, as it is shown in FIG. 5, and with a round arch wire retained in the slot.

In this specification and the appended claims, for convenience in language the brackets, buccal tubes and parts thereof are referred to, unless otherwise specified, as they would be used mounted in the upper arch region of a patient's mouth, especially in the case of brackets, since those described are intended primarily for use in lingual procedures. However, both the brackets and the buccal tubes may be used for either labial or lingual procedures. As applied to the bracket structure the labial and lingual direction designations are reversed between the two procedures, e.g. the bracket surface referred to as the labial surface in the labial procedure becomes the lingual surface in the lingual procedure, and vice versa, and the arc wire slot opens to the lingual and not the libial. Again for convenience description the brackets are described as having specific named surfaces but, as will be apparent, smooth exterior contours can only be achieved by avoiding sharp edges and sharp edged junctions wherever possible, and the various surfaces therefore usually merge smoothly with one another without a definite junction between them being apparent.

Similar parts are given the same reference number in all the Figures of the drawings wherever this is appropriate.

The brackets of the invention as described and shown herein are intended for use with the so-called straight wire technique with which each bracket is attached to its respective tooth in an attitude such that, as the arch wire attempts to return to its preformed arch shape and to be straight as seen in a mesial-distal, labial-lingual plane, the tooth is moved toward its desired optimized position and attitude. In order for the arch wire to be straight at the conclusion of the procedure the brackets for different teeth must accommodate the very different inclinations of the tooth surfaces to which they are attached. There are two main methods by which this is done, either by suitable shaping of the bracket bases and of their base surfaces that contact the teeth surfaces, or by changing the inclination of the arch wire slots. In the brackets shown herein all of the torque requirements (rotation about a mesial distal axis), angulation requirements (rotation about a labial lingual axis), and first order preadjustments, are obtained by suitable shaping of the bracket bases, particularly of the surface that engages the tooth surface, and by variation of the base thickness, so that when the teeth are in their optimum attitude and rotational position all of the slot surfaces engaged by the arch wire are aligned. The other method of slot inclination can also be used in the brackets of the invention, either alone or in combination with the first-described method. However, when the other method is used, with some brackets the inclination of the slot may be so extreme that, for example, in a bracket fixed to the lingual surface of a central incisor no attempt is made to have the slot remain parallel with the labial lingual axis and instead it opens to the occlusal parallel to the gingival occlusal axis (as viewed from the mesial or distal); nevertheless such a bracket is within the scope of the language of the appended claims.

The brackets shown in FIGS. 1 through 15 are intended specifically for use in lingual procedures and are active, comprising an internal attitude controlling spring that engages the arch wire, at least while the tooth is in a non-optimum attitude and position, so that they inherently permanently attempt to control the attitude of the bracket relative to the arch wire. In practice the use of brackets with such integral spring mediated attitude control is virtually essential for labial procedures, since external protrusions, such as the gingivally-occlusally protruding tie wings usually provided with lingual procedure brackets to retain elastomeric ligatures thereon, are neither practical nor desired. The brackets of FIGS. 16 through 19 are only usable in the standard labial procedures because of the presence of such external tie wings, and although incorporating an attitude controlling spring of the invention, are also externally ligatable when required or desired, and such brackets may be preferred by some orthodontists. For example, situations may arise in a procedure that require the use of an external ligature additional to, or even replacing, the attitude control provided by the spring member, for example where initially a tooth is so grossly displaced that it is not possible to engage the arch wire in the slot or, if engaged, it is not possible to hold the slot closed without over stressing the spring member and/or the arch wire. Another consideration is that orthodontists who previously have only been using external ligatures in their procedures may be somewhat reluctant initially to adopt a bracket involving a completely new procedure, and which does not permit them at least the opportunity of using their established skills, and are reassured if provided with a bracket that while including an attitude controlling spring also has provision for an external ligature.

Figure 10:
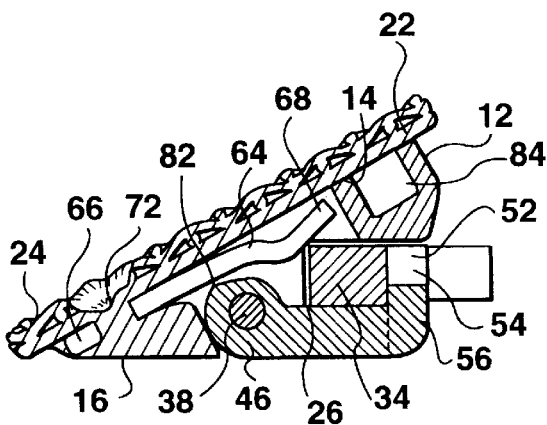
FIGS. 10 and 11 are cross sections similar to FIG. 5 showing a bracket in use with arch wires respectively of rectangular and quarter round cross section.
Figure 11:
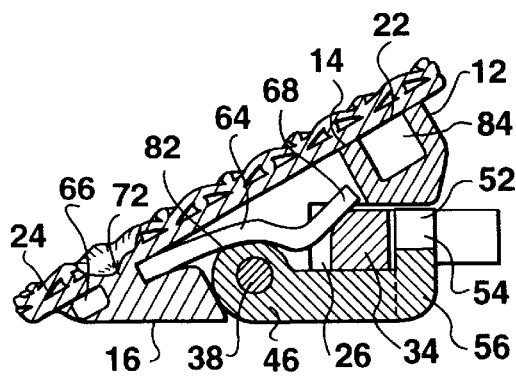

Referring now to the brackets shown in FIGS. 1 through 14, each bracket body has labial, lingual, gingival, occlusal, mesial and distal surface portions 10, 12, 14, 16, 18 and 20 respectively, the corresponding orientation directions, except for the mesial and distal, being shown in FIG. 3 by corresponding arrows. Each bracket is attached, as for example by laser welding along its edges, to the gingival surface of a base 22 consisting of a thin metal foil, the base in turn being attached to the gingival surface of a metal wire mesh 24, the open pores of which facilitate the attachment of the bracket to a tooth by cement in providing spaces to receive the cement. Thus, all of the brackets are shown as ready for mounting on the respective tooth by cementing, as increasingly is preferred, although they could also be mounted by the older method of attaching them to respective tooth-embracing bands, which method is not illustrated. The body is provided with a mesial-distal extending arch wire receiving slot 26 having its lingual side open, the slot in this embodiment being of rectangular transverse cross section in a gingival-occlusal, labial-lingual plane and having labial, gingival and occlusal surfaces 28, 30 and 32 respectively. The slot receives an arch wire 34 (see FIGS. 5, 6, 10 and 11), which usually in the early stages of a procedure is of circular cross section (FIGS. 5 and 6), and of small enough diameter for the bracket to slide freely along it once the arch wire is fully within the slot and fully aligned therein. Subsequently the round arch wire usually is replaced by one of D-shape cross section (FIG. 10) or rectangular cross section (FIG. 11).

Means for retaining the arch wire in the slot, and releasing it when required, consist of a slot closure member indicated by arrow 36 that takes the form of a self-jamming shutter, the member being mounted by a mesially-distally extending pivot pin 38 that passes through the closure member and the bracket body so that the member is movable about pivot axis 40 of the pin between a slot open position (shown for example in FIGS. 2 and 7), in which the open lingual slot side is unobstructed and therefore open, and a slot closed position (shown in FIGS. 1, 4–6, and 10–15), in which the closure member closes the open lingual slot side. The bracket body is provided with a centrally disposed rectangular recess 42 that opens centrally to the body occlusal surface portion 16 and also centrally to the part 44 of the lingual surface portion 12 between the arch wire slot 26 and the junction between the occlusal and lingual surface portions, this part 44 thus being divided into two equal mesial distal spaced sections by the intervening recess. The jamming shutter consists of a pivot portion 46 that is always within the recess 42, and through which the pivot pin 38 passes, and a slot closure portion 48 (indicated in FIG. 3 only by arrow 48) the latter being movable with the pivot portion. The slot closure portion extends mesially-distally with respect to the device body and is the portion of the slot closure member that closes the open side of the arch wire slot, and also retains it in the slot closed position, as will be described below. The part of the pivot portion between it and the closure portion 48 extends lingually-labially and for convenience is designated as an arm portion 50, this arm portion moving into and out of the recess 42 respectively as the slot closure member is moved toward and away from the slot closed position. The slot closure portion consists of a slot closing part 52, which in this embodiment is divided into two mesially-distally spaced sections by an intervening rectangular slot 54 having its longer dimension extending mesially-distally, and a bracket body engaging part 56 that extends equally mesially and distally from its centrally disposed junction with the lingual end of the arm portion. The mesial-distal dimensions of both the slot closing part 52 and the body engaging part 56 are equal to the corresponding mesial-distal width of the bracket body, so that in the slot closed position the mesial and distal surface portions of the two parts are flush with the mesial and distal surface portions 18 and 20 of the bracket body.

The dimensions of the bracket body and of the slot closure member are such that as the slot closure member is moved about the pivot axis 38 toward the slot closed position, at first spaced sections of the slot closing part 52 rub tightly against the corresponding immediately adjacent sections of the bracket body lingual surface portion 44 with an interference fit rubbing and butting engagement between them, such that the two sections of part 52 are flexed toward the lingual against the elasticity of the material of the two sections. As the slot closure member moves further toward the slot closed position this first rubbing engagement is succeeded by similar tight rubbing and butting engagement between the two spaced sections of the body engaging part 56 and the corresponding immediately adjacent sections of body portion 44. The two mesially-distally spaced sections of the lingual surface portion 44 also have an interference fit between their engaged rubbing and butting surfaces and the corresponding immediately adjacent engaged rubbing and butting surfaces of body engaging part 56, such that the two sections of part 56 are also flexed toward the lingual against the elasticity of the material of the body engaging part, so that they are jammed against the body portion sections 44, hence the reference to the slot closure member as a jamming shutter that closes the arch wire slot. The result is that upon such first rubbing engagement the closure member cannot be moved any further in the slot closing direction without the exertion of sufficient force to flex in the lingual direction first the slot closing part sections 52, and then the two end sections of the body engaging part 56. The slot closure part sections 52 will usually be a little more flexible than the body engaging part sections 56 because of the presence of the slot 54, so that the closing force required will increase progressively as the slot closure member moves into the slot closed position and the rubbing butting engagement of sections 52 is replaced by the rubbing butting engagement of sections 56. Once in the slot closed position the moving sliding interference fit engagement between the surfaces of sections 56 and those of surface portion sections 44 becomes a stationary butting interference fit engagement between them, with the butting sections of the body engaging part 56 permanently flexed lingually outward from the bracket body to provide a corresponding labially-directed retaining force. Such butting engagement therefore positively retains the slot closure member in the slot closed position, and movement thereof from that position requires correspondingly forceful flexing of the body engaging part 56, and thereafter of the slot closing part 58, in a the lingual direction away from the bracket body against the resilience of the material of the body engaging part as it slides over the bracket body lingual surface portions 44.

Such an effective method of retaining the slot closure member is completely feasible with a product such as an orthodontic bracket in that the number of openings and closings it is likely to experience during its working life is relatively limited, so that the possibility of wear of the sliding engaging surfaces is minimal. Orthodontic brackets are already of necessity manufactured to very close tolerances (e.g. 0.00025 mm or 0.0001 in) so that the required rubbing, butting and jamming interference fit can easily be achieved. For example, in a bracket of the invention having a mesial distal dimension (not including the base 22 or mesh 24) of 2.47 mm (0.099 in) and a gingival occlusal dimension of 3.05 mm (0.112 in), the slot closing part sections 52 will measure occlusally-gingivally about the same as the arch wire slot (slightly less is possible as is also slightly more so that it engages the body gingivally of the slot to provide a positive stop, while the bracket body engaging part sections 56 of the jamming shutter will usually measure 0.42 mm (0.017 in) occlusally-gingivally. The total mesial-distal length of the part 56 will be equal to that of the bracket, while the mesial-distal lengths and labial-lingual thicknesses of the end sections 56 is dependent upon the amount of flexing found to be necessary for the material used for the bracket body. Thus, the mesial-distal lengths can in this case vary between 0.45 mm (0.018 in) and 0.925 mm (0.037 in), while the labial-lingual thickness can vary between 0.175 mm and 0.425 mm (0.007 in and 0.017 in); the amount of flexing required of the end sections is of the order of 0.005–0.01 mm (0.0020–0.004 in), and usually about 0.0075 mm (0.003 in), the elasticity of the material being such that the sections fully recover upon their disengagement from the bracket body. The amount of the deflection should not exceed the yield point to prevent permanent deflection of the sections. A suitable material for the bracket is 17/4PH stainless steel. In the event that some brackets of a batch are found to open and close too easily this can be corrected by the application of a very thin (e.g. 0.0025 mm or 0.001 in) hard adherent coating to one or both of the engaging jamming surfaces.

In this embodiment the movement of the slot closure member from slot closed to slot open position is produced with the aid of the recess 52, which constitutes a tool-receiving recess elongated in the mesial-distal direction, into which the operator inserts the flattened end 58 (FIG. 4) of an opening tool which, upon rotation in the direction of the arrows 60 in FIG. 4, moves the slot closure member in the occlusal direction from the slot closed position. A twist rotation of the tool of only about 45° is sufficient to move the slot closure member to the slot open position, no special instrument being required to move the closure member to the slot closed position. The gingival-occlusal dimension (height) of the slot can be as small as 0.25 mm (0.010 in) and its outer edges can be rounded so that it is impossible for a patient to gain a purchase with a fingernail to open the bracket; typically an adult fingernail is on average 0.4 mm (0.016 in) thick, while a thumbnail is usually on average 0.5 mm (0.020 in) thick. The labial-lingual length of the slot gingival surface 30 is greater than the corresponding length of its occlusal surface 32 by an amount equal to the labial-lingual thickness of the slot closure part 50 and the body engaging part 56, so that the resultant overhanging part of the slot gingival surface 30 provides a positive stop for the slot closure member against which it buts to establish its fully closed position. In this embodiment the junctions 62 between intervening arm portion 50 and the body engaging part 56 are of reduced mesial-distal dimension to thereby increase the effective lengths of the body engaging sections of part 56 available for said flexing. In slot closed position the lingual surface of the slot closure portion is flush with the corresponding lingual surface portion 12 of the bracket body, and similarly the occlusal surfaces of the pivot portion 46 and slot closure portion 48 are flush with the corresponding occlusal surface portion 16 of the bracket body, so that in such position the bracket presents smooth, solid exterior surfaces that minimize the likelihood of rough contact between the brackets and the tongue and adjacent tissue of the mouth.

Figure 7:
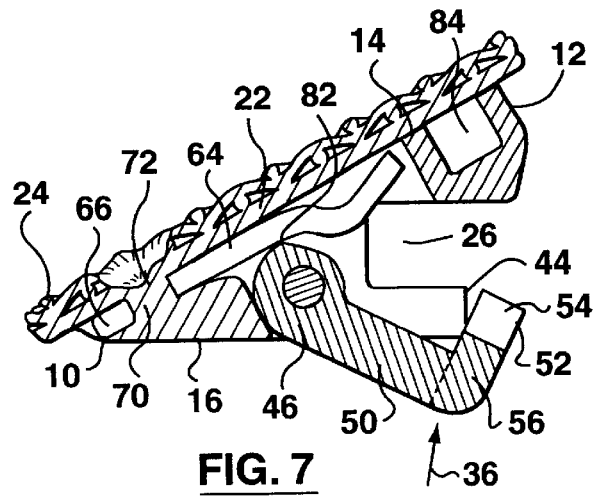
FIG. 7 is a cross section similar to FIG. 5 with the slot closure member in slot open position and without an arch wire in the slot.
Figure 12:
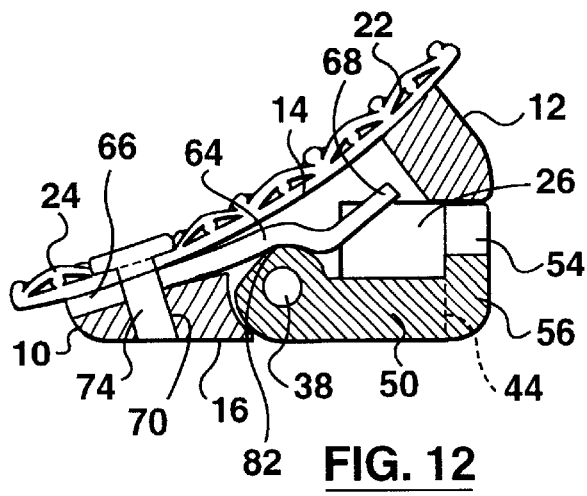
FIG. 12 is a cross section similar to FIG. 5 of another embodiment showing an alternative method of retaining an attitude controlling spring in the bracket body.

The brackets as so far described are "passive", in that the only control of tooth movement they could provide is by the interaction produced by contact between the arch wire and the walls of the slot 26 through which the wire passes. It is preferred in most procedures that the brackets be "active", i.e. that they include some inherent means for controlling the attitude of the bracket relative to the arch wire, and to that end each is provided within the recess 42 with a flat attitude controlling spring member 64 having a fixed end portion 66 that is fixed rigidly to the bracket body and a free end portion 68 extending into the arch wire receiving slot for engagement in a mesial-distal, labial-lingual plane with an arch wire 34 in the slot, such engagement urging the arch wire toward the labial surface of the slot closure part and the occlusal surface of the slot. The spring may be inserted in the bracket as it is assembled with the fixed end portion of the spring member sandwiched between the bracket body and the foil member 22, the spring being provided with a through aperture 70 and it, the bracket body, the foil member 22 and the mesh layer 24 being attached to one another simultaneously by upsetting a portion 72 of the bracket body and/or the foil member and/or the mesh layer into the through aperture, as is shown in FIGS. 5, 7 10 and II. FIG. 12 shows an alternative method of fastening the separate components together, comprising a rivet 74 in place of the upset portion 68.

Figure 8:
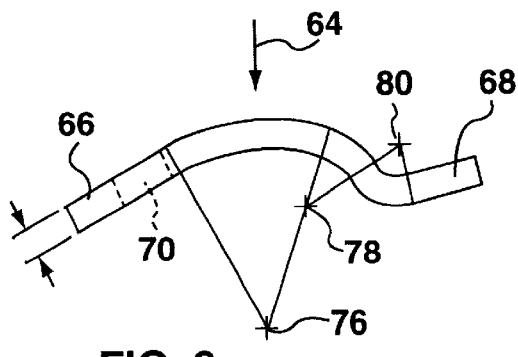
FIG. 8 is a view in elevation from the mesial or distal of an attitude controlling spring pre-formed ready for incorporation into a bracket.
Figure 9:
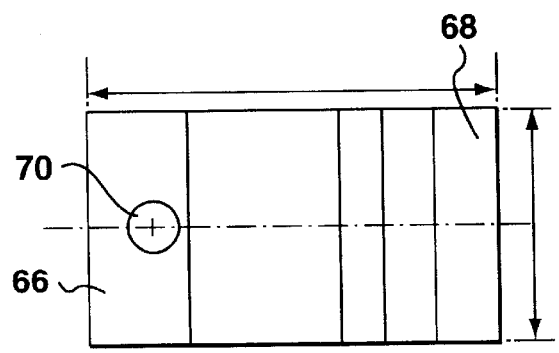
FIG. 9 is a plan view of the spring of FIG. 8.

FIGS. 8 and 9 show a typical shape for such a spring before its assembly into the bracket, the fixed end portion containing the aperture 70 being flat, while the free end portion comprises a first part that is concave toward the occlusal about two different centers 76 and 78, followed by a part that is convex toward the occlusal about a center 80, and terminating in the part that engages the arch wire, this terminating part again being flat. The force with which the spring engages an arch wire is dependent on the cross section dimension of the arch wire, and the dimensions of the spring, particularly its width and thickness; it can also be adjusted by forming the spring with different amounts of preloading before the bracket is assembled, for example by adjustment of the profile of the spring, the force increasing as the radii of curvature about the axes 76–80 are decreased, and vice versa. A preferred material for the springs used in the orthodontic devices of the invention is the family of nickel-titanium alloys, commonly referred to as superelastic shape recovery metal alloys, in that they can withstand without damage strains of as high as about 6–8%, as compared to the usual maximum for stainless steels, the materials most commonly previously used, of about 0.5%. There is now adequate literature available as to the performance and fabrication of springs using these materials and further explanation is not required herein. Stainless steels of the required qualities will continue to be the material of choice for the device body and the jamming shutter.

FIGS. 5 and 6 show the bracket used in conjunction with an arch wire of round cross section, FIG. 6 showing a typical curvature for the wire in the mesial distal plane. The wire contacts the slot closing part 52 at two mesially distally equally spaced points A and is in turn contacted by the spring 64 at a point B centrally between the points A. No change in the contacts between the arch wire and the spring can take place without deflecting the spring labially away from its most lingually forward position. FIG. 10 shows the use of the bracket with an arch wire of rectangular cross section and of the largest dimensions (0.021 in×0.025 in) that can be fitted in the slot; this gives a high degree of torque control with the spring providing a strong braking action against mesial-distal sliding. FIG. 11 shows the use of the bracket with an arch wire of quarter round cross section and of somewhat smaller dimension (0.020 in); this gives full attitude control about all reference axes which pass through the arch wire slot centroid while at the same time permitting low friction mesial distal sliding. As will be seen from FIGS. 10 and 11 the free end portion of the spring member may be spaced from the pivot portion 46 of the slot closure member (FIG. 10) or may engage the adjacent surface of the pivot portion (FIG. 11). Preferably this engaged adjacent surface comprises a cam surface that is shaped to have a protruding lobe 82 that, when the slot closure member is in slot open position, as shown in FIG. 7, engages the spring free end portion and moves it out of the arch wire receiving slot and thus out of contact with the arch wire, facilitating both insertion and removal of the arch wire into and out of the slot during the course of a procedure. There is a resultant tendency for the spring acting on the cam lobe 82 to urge the slot closure member toward the slot closed position, but this is resisted sufficiently by the initial rubbing engagement of the slot closing part sections 52 with the corresponding lingual surface portion sections 44, so that the effect is to hold the slot closure member in a suitable open position without moving too far toward the occlusal, while preventing it from opening wider than is necessary. This positive closing tendency does mean that once the arch wire is placed on the slot closure member it is "scooped" into the arch wire slot simply by moving the slot closure member to slot closed position. Orthodontists often require a bracket to have a supplementary mesial-distal extending slot or passage for use with a second arch wire or with other appliances, and such a slot 84 is readily provided in the brackets of the invention in the part of the bracket body close to the lingual surface portion between the slot and the gingival surface portion, as will be seen from FIGS. 5, 7, 10 and 11.

Figure 13:
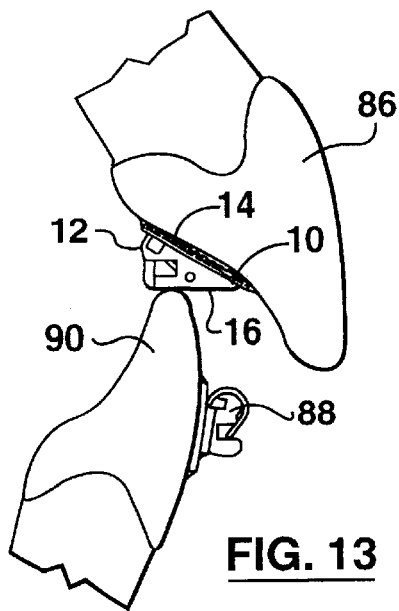
FIG. 13 is a view in elevation from the mesial of opposed upper and lower incisors with a bracket as illustrated by FIGS. 1–12 cemented to the lingual surface of the upper tooth and a conventional Hanson SPEED bracket cemented to the labial surface of the lower tooth, the teeth being in a position corresponding to a typical deep-bite malocclusion prior to the commencement of an orthodontic correction procedure.
Figure 14:
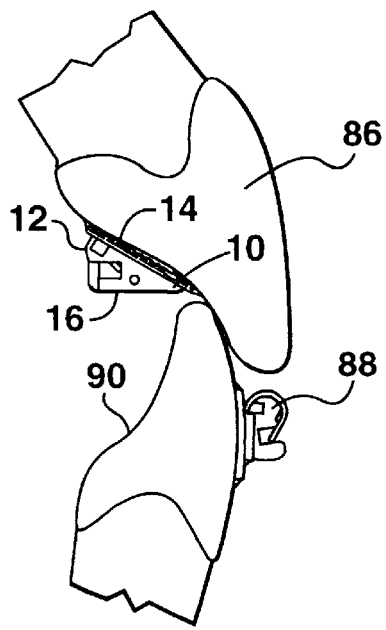
FIG. 14 is a view similar to FIG. 13 showing the position of the teeth at the conclusion of a successful procedure.

The brackets shown and described in association with FIGS. 1–12 are intended for attachment to the lingual surface of an incisor or canine tooth, which are characterized in that their labial-lingual dimension increases progressively from the gingival to the occlusal. FIGS. 13 and 14 show a typical application for such a bracket attached to the lingual surface of an upper incisor 86 for use in a lingual procedure, while a standard Hanson SPEED system bracket 88 is attached to the labial surface of the opposed lower incisor 90 for simultaneous use in a labial procedure. FIG. 13 shows a common problem encountered in that the patient has a deep-bite malocclusion in which the lower incisor is set too far lingually from the upper incisor for the teeth to meet properly when the jaw is closed, so that the bite is deeper than it should be. The brackets of the invention are particularly suited for use with such a problem in that the gingival-occlusal dimension of the bracket body decreases progressively from the lingual to the labial, and this decrease has been made to correspond approximately to the average increase in dimension from the occlusal to the gingival of an incisor or canine tooth. It will be seen that with the bracket attached to such a lingual surface the labial-lingual dimension of the bracket-tooth combination is at least approximately uniform from the occlusal to the gingival, so that the bracket occlusal surface lies in a mesial-distal, labial-lingual extending plane. This, together with the fact that in the slot closed position the occlusal surface portion of the slot closure member 48 is flush with the occlusal surface portion 16 of the bracket body means that the bracket is thereby able to provide a combined occlusal surface which is unobstructed and can constitute a bite plane against which the cutting edge of the lower tooth 90, i.e. at the junction of its occlusal and labial surface portions, can engage during biting action. FIG. 14 shows the incisors 86 and 90 in their ideal relationship when the malocclusion has been corrected and it will be noted that the lower incisor no longer engages the lingual bracket. This structure therefore has a number of practical advantages. The lingual brackets function as bite planes to prevent the lower incisors from reaching their usual deep-bite malocclusion over-closure, and can therefore replace the acrylic bite plates that are placed in the mouth to correct this. They also operate similarly to prevent any interference with the brackets 88 on the lower teeth while the malocclusion is present, so that they can be bonded to the teeth without fear that they will be detached as a result of over-biting. It also permits the posterior teeth to be erupted during the procedure to further reduce the overbite.

Figure 15:
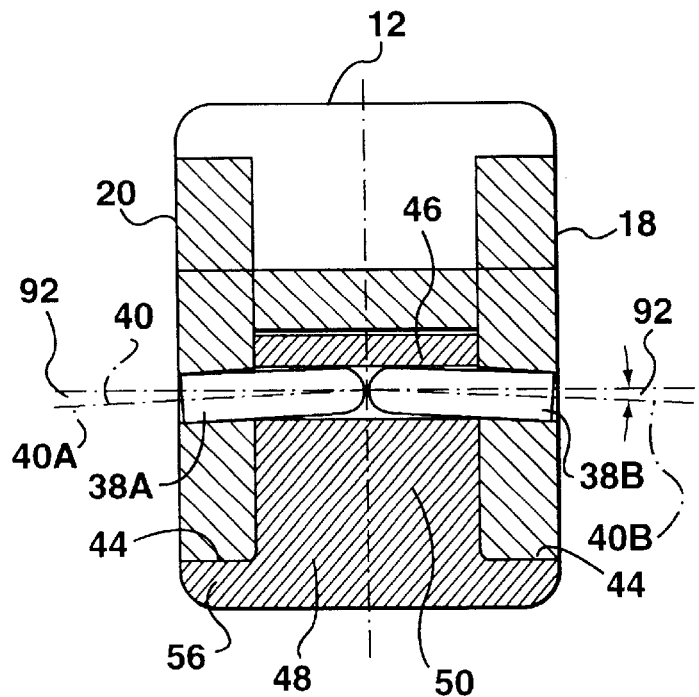
FIG. 15 is a cross section in a mesial-distal, labial-lingual plane through a further embodiment showing an alternative structure of a hinge pin for the slot closure member.

FIG. 15 shows an embodiment in which the structure of the pivot pin 38 is changed from that shown in the embodiments of the preceding Figures to assist in retaining the slot closure member in the slot closed position. The pin is divided midway along its length into two equal-length parts 38A and 38B, and the respective axes 40A and 40B of the pin parts are inclined in the mesial-distal, labial-lingual plane at a small angle 92 (e.g. up to about 3°) from the mesial-distal axis 40 toward the labial, the bore in the pivot portion 46 that receives the pin parts being sufficiently large that with the slot closure member in the slot open position the pin parts are straight, or nearly so (the amount of any such bending that may be present being far too small to be shown in the drawing), while with the member in the fully slot closed position the ends of the pin parts within the pivot portion bore are bent toward the lingual and press against the labial part of the bore wall, thereby supplementing the jamming engagement of the slot closure member with the bracket body. A typical diameter for the inclined holes in the bracket body is 0.30 mm (0.01 2 in), and the pin parts will be slightly oversize so that they must be forced into the holes and then secured against working free by laser welding their outer ends to the bracket body. The two pin parts are therefore operative to urge the body engaging part 56 into its desired inference engagement with the lingual surface portion parts 44 and will flex toward the lingual as the slot closure member is moved to the slot open or slot closed position; the adjacent ends of the two pin parts are rounded and spaced from one another to permit this flexing movement to take place. The flexing that takes place as the slot closure member is moved, and the flexing that is required to maintain the slot closure member securely in the fully slot closed position, is shared between the two sections of the body engaging part 56 and the two pin parts 38A and 38B, in a ratio determined by their respective applicable dimensions and the elasticity of their respective materials. In a bracket intended for labial procedures the pivot pin sections will be inclined oppositely. Although such a structure is slightly more complicated it is able to accommodate the use of body parts with somewhat greater manufacturing tolerances than structures with a single straight pin, which otherwise might require some additional manufacturing step, such as the post-assembly coating described above. In addition, or alternatively, it enables the use of much stiffer materials for the slot closure member and/or bigger labial-lingual dimensions for the body engaging part 56. In addition, or alternatively, it can help to ensure that the materials used are not stressed beyond their elastic limit, although the use of the more expensive high elasticity nickel/titanium alloys mentioned above for the small pin parts will ensure that this cannot happen to them.

Figure 16:
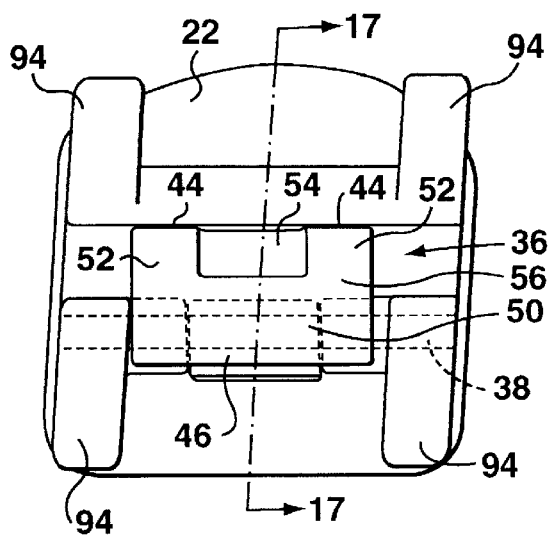
FIG. 16 is a view in elevation from the labial of a further embodiment showing the application of the invention to a bracket structure of the so-called siamese twin type.
Figure 17:
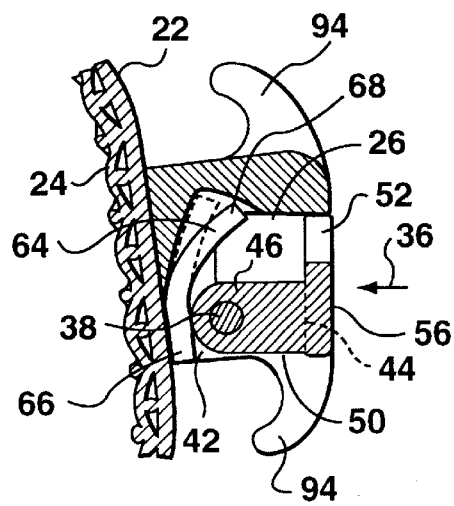
FIG. 17 is a gingival-occlusal longitudinal cross section taken on the line 17—17 in FIG. 16.
Figure 18:
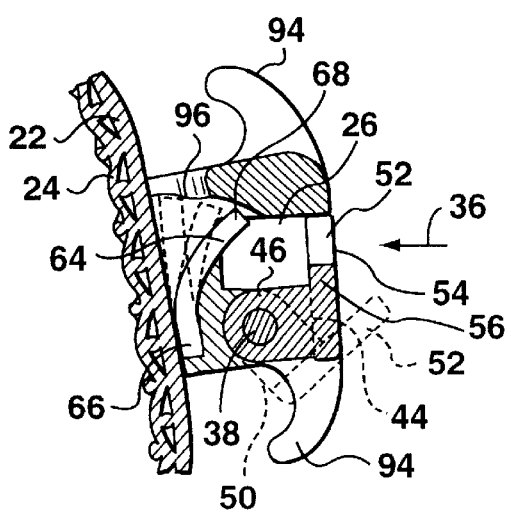
FIG. 18 is a longitudinal cross section similar to FIG. 17 of a siamese twin type bracket incorporating an attitude controlling spring that is a further embodiment of the invention.
Figure 19:
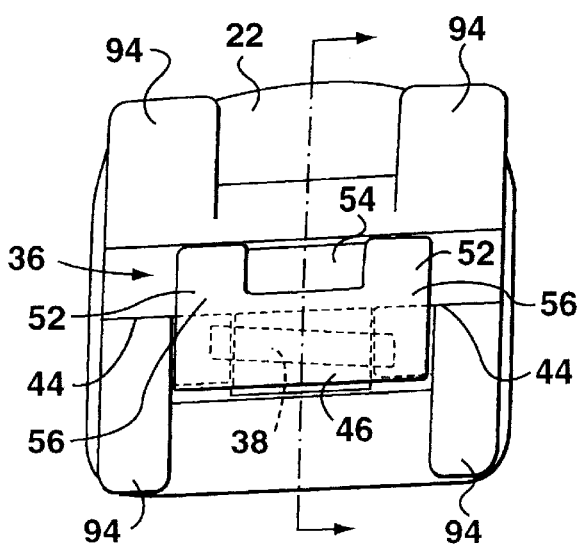
FIG. 19 is an elevation similar to FIG. 17 of a further embodiment.

The structures of the invention are also applicable to brackets of the type commonly used for labial procedures, and FIGS. 16–19 show examples of their application to the type of bracket usually referred to as a siamese twin bracket. Such a bracket is provided with two mesially-distally spaced pairs of tie wings 94 for the reception and retention of an external ligature, such as a soft metal wire or an elastomeric hoop or loop, and for the anchoring of tension and compression members. The manner in which such orthodontic elements are used is well known and does not require illustration or further explanation. The slot closure member 36 is disposed between the tie wings and operates exactly as described above for the brackets intended for lingual procedures. The bracket body and its bonding base are of known rhomboidal shape, as seen from the labial and lingual, the mesial and distal faces being inclined at a small angle to a neutral gingival-occlusal extending plane. The use of such rhomboid shaped brackets is preferred by many orthodontists and is now well established. Because of the inclination the slot closure member is offset toward the mesial, as seen in FIG. 16, to prevent it fouling the distal occlusal tie wing as it is moved to slot open position. Preferably the bracket is made active by incorporating therein between the bracket body and the base 22 a short curved attitude controlling spring 64 whose profile can be adjusted as required to provide any desired amount of pre-load. The active bracket shown in FIG. 18 includes provision to de-activate the ligating spring 64 if desired; this is accomplished by pressing the spring hard lingually toward the mounting base until its free end is engaged behind a mesially-distally extending ledge 96, from which inactive position it can be retrieved as required by hooking the free end forward using the point of a standard scaler. In the bracket shown in FIG. 19 the slot closure member is also of rhomboid shape so that offset thereof, as with the embodiment of FIG. 16, is not required. This does mean however that the pivot pin 38 must be inclined at the same angle, and must be made shorter, so that the bore in which it works does not intrude into the arch wire slot. Such a bracket is best assembled by making the body as two mirror image parts with registering blind bore holes, the two parts being placed together with the pin between them and then welded together along their butting edges.

Figure 20:
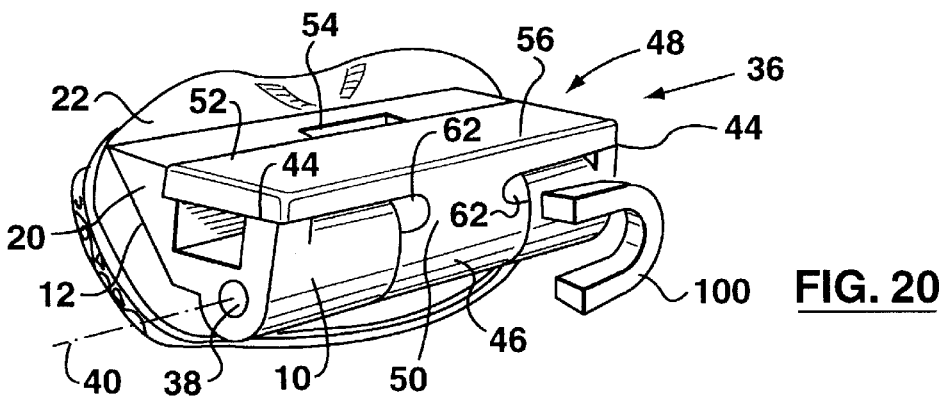
FIG. 20 is a perspective view from the distal-occlusal of a further embodiment comprising a convertible buccal tube with its slot opening to the occlusal.
Figure 21:
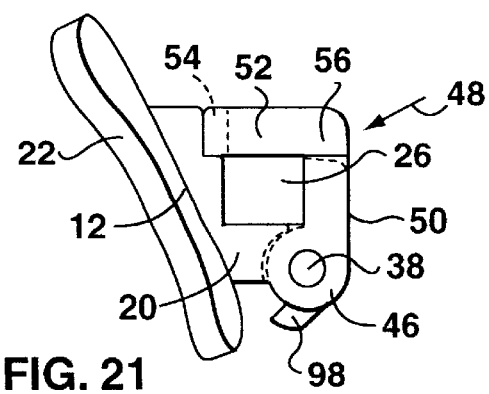
FIG. 21 is a view in elevation from the distal of the buccal tube of FIG. 20 with its slot closure member in slot closed position.
Figure 22:
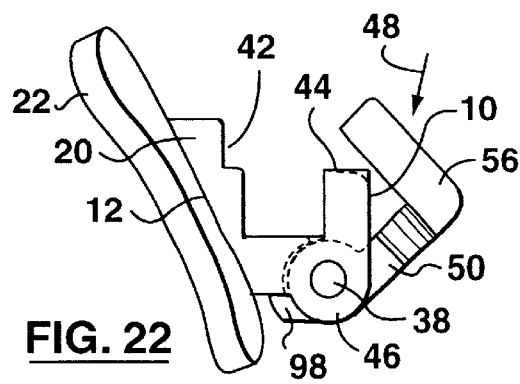
FIG. 22 is a view similar to FIG. 21 with the slot closure member in slot open position.
Figure 23:
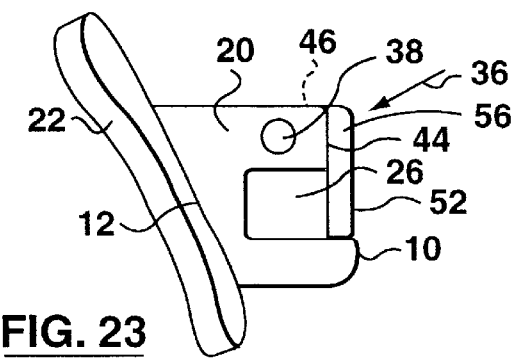
FIG. 23 is view similar to FIG. 21 of a buccal tube with its slot opening to the labial.
Figure 24:
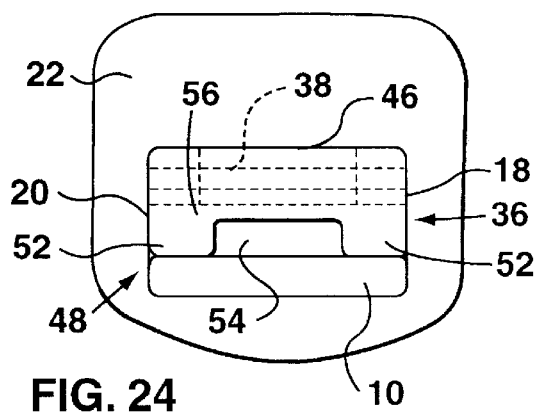
FIG. 24 is a view from the labial of the buccal tube of FIG. 23.
Figure 25:
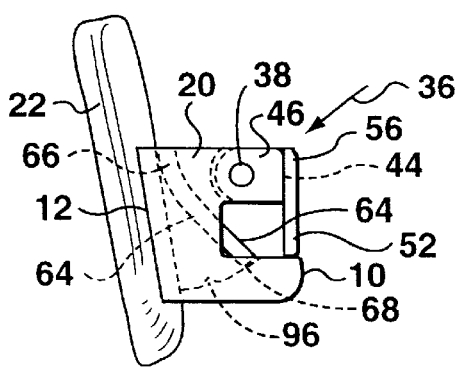
FIG. 25 is a view similar to FIG. 23 showing the inclusion of an attitude controlling spring within the tube to render it active.
Figure 26:
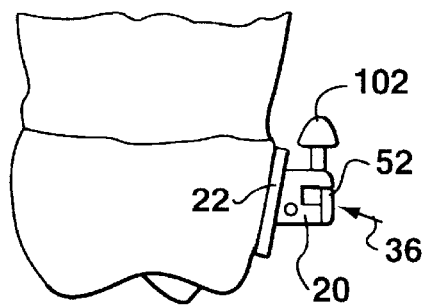
FIG. 26 is a view in elevation from the mesial showing the buccal tube of FIGS. 23 and 24 mounted on the labial surface of an upper first molar tooth, and showing an alternative structure for the attachment of elastic members thereto.

FIGS. 20 through 29 show the application of the invention to provide new convertible buccal tubes, those illustrated by FIGS. 20–24, 26 and 29 being passive. Those shown in FIGS. 20–24 are intended for mounting on the labial surface of a lower right first molar and have the arch wire slot 26 opening to the occlusal. The function and operation of the slot closure member 36 (jamming shutter) in its movement between slot open and closed positions, and in its positive retention in the slot closed position by the elasticity of the slot closing part sections 56, is exactly the same as described above for the orthodontic brackets. Since in the tube of FIGS. 20–22 the slot closure member moves labially and gingivally it is provided with a mesial-distal extending tail part 98 that engages the bracket body to ensure that it cannot open too far. One other difference in structure with the tube of FIGS. 20–22 is that the slot 54 receiving the shutter opening tool 58 is provided in the body of the tube and not in the slot closure member. As with the lingual brackets, in the slot closed position the occlusal surface of the slot closure portion 48 is flush with the occlusal surface portion of the bracket body to provide a smooth surface. Provision must usually be made for the attachment to selected brackets of traction springs, elastic hoops and other devices used in orthodontic procedures, and this may comprise a member, such as a hook 100 shown in FIG. 20, which can readily be attached to the fixed portion of the tube body in a location where it will not foul the slot closure member as it is moved between positions. An examination of FIGS. 13 and 14 will show that it is difficult to provide such attachment members with the labial brackets first described, and this problem may be resolved by employing a convertible buccal tube of the invention, which can be an active tube as described below, in place of a bracket FIGS. 23 and 24 also show a passive convertible buccal tube of the invention intended for cementing to a lower right first molar, but in this case the arch wire opens to the labial, as with a bracket. The slot closure member pivots about the pin 38 towards the labial and then toward the occlusal and does not require any means, such as the tail part 98, to restrict the amount by which it opens. FIG. 25 shows an active convertible buccal tube intended for mounting on a lower second bicuspid, so that its labial-lingual dimension varies less than with the previously-described tubes. The tube is made active by the inclusion within the tube body of a short curved attitude controlling spring 64 that extends gingivally and protrudes into the arch wire slot at the junction of its lingual and gingival surfaces. The spring can be disengaged, so that the tube is passive, by pressing it lingually until its free end engages behind a mesially-distally extending ledge 96, as with the siamese twin bracket of FIG. 18. FIG. 26 shows another form of attachment device for the buccal tube of FIGS. 23–25, consisting of a mushroom-headed post 102 onto which tension members such as springs and elastomeric loops can be anchored.

Figure 27:
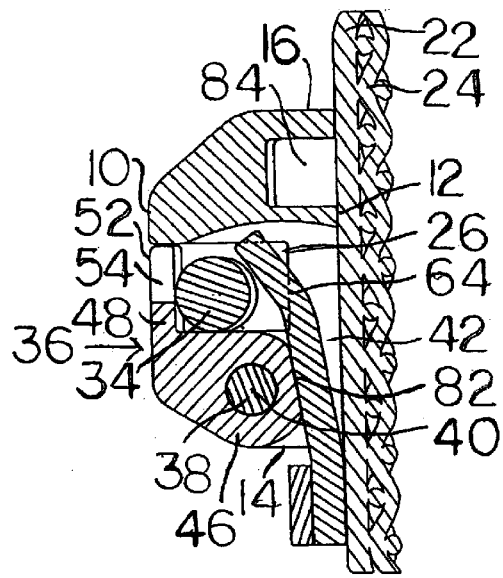
FIG. 27 is a labial-lingual, occlusal-gingival cross section through an active convertible buccal tube in which an attitude controlling spring also assists in retaining the slot closure member in slot closed position.
Figure 28:
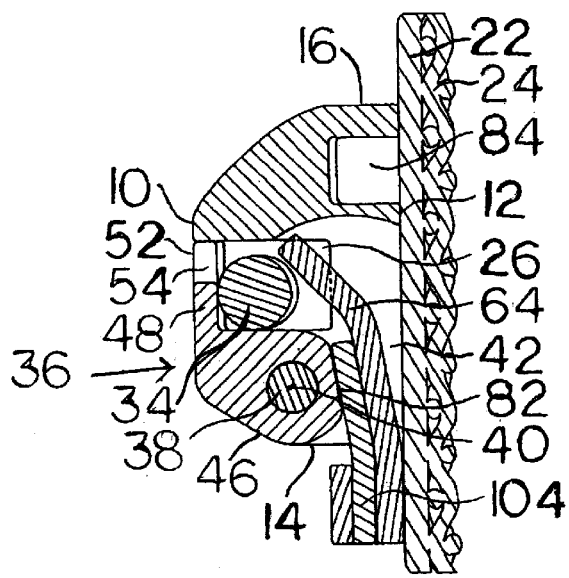
FIG. 28 is a cross section similar to FIG. 27 of an active convertible buccal tube provided with separate attitude controlling and closure member retaining springs.
Figure 29:
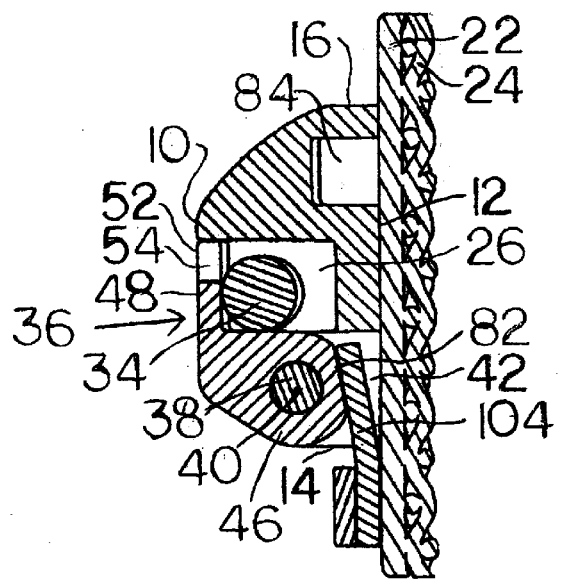
FIG. 29 is a cross section similar to FIG. 27 of a passive convertible buccal tube provided with a closure member retaining spring.

The convertible buccal tubes shown in FIGS. 27–29 are intended for use with lower left central incisors and the jamming shutters thereof open by moving to the lingual and gingival. The tubes are somewhat larger in gingival-occlusal dimension than those of FIGS. 20–26 to permit the provision of a supplementary mesial-distal extending slot 84, so that they are closer in construction to a bracket than those prior buccal tubes. It may also be noted that in the convertible tubes of FIGS. 20–26 any arm portion 50 is very short in length, to the extent that it has become almost vestigial; in the tubes of FIGS. 27–29 the slot closure portion 48 merges with the pivot portion 46 without an intervening arm portion. In the active convertible tube of FIG. 27, as with the bracket of FIGS. 1–12, the attitude controlling spring 64 engages a cam surface 82 of the pivot portion 46 and cooperates therewith to assist in holding the jamming shutter in the slot closed position, and is moved by the cam surface as the slot closure member is moved toward the slot open position out of the arch wire slot to ensure that it is disengaged from any arch wire 34 therein, so that the arch wire can more easily be removed and inserted. In the convertible tube of FIG. 28 a short auxiliary spring 104 with a predetermined amount of preload bears against the cam surface 82, and this spring backs up the effect of the attitude controlling spring 64, which is only fully operative for this purpose when the tube is empty or when an archwire is not deflecting it lingually. The slot closure member cannot be moved toward the slot open position without deflecting at least the auxiliary spring. The tube of FIG. 29 is passive in the absence of an attitude controlling spring, but is still provided with the auxiliary spring 104 engaging the cam surface 82 for the action described above.

I claim:

1. An orthodontic device comprising:
   a device body having labial, lingual, gingival, occlusal, mesial and distal surface portions, the body having therein a mesial-distal extending arch wire receiving slot having one side open to a respective device body surface portion to permit insertion of an arch wire into the slot, and
   a slot closure member mounted by the device body so as to be movable about a pivot axis between a slot open position in which the open slot side is open, and a slot closed position in which the closure member closes the open slot side to retain an orthodontic arch wire in the slot;
   wherein the slot closure member comprises:
      a pivot portion mounted by the device body for the pivoting movement of the slot closure member about the pivot axis; and
      a slot closure portion movable with the pivot portion and extending mesially-distally with respect to the device body; and
   wherein the slot closure portion comprises:
      a slot closure part that in the slot closed position closes the open side of the arch wire slot; and
      at least one mesially-distally extending body engaging part that in the slot closed position of the slot closure member engages with an adjacent surface portion of the device body with an interference fit butting engagement between them providing a retaining force such that the slot closure member is retained thereby in the slot closed position, and such that movement of the slot closure member into the slot closed position requires flexing of the body engaging part in a direction away from the device body against the elasticity of the material of the body engaging part.

2. An orthodontic device as claimed in claim 1, wherein there is provided within the bracket body a flat attitude controlling spring member having a fixed end portion fixed to the bracket body and a free end portion extending into the arch wire receiving slot for engagement in a mesially-distally extending plane with an arch wire in the slot, such engagement urging the arch wire toward the slot closure part.

3. An orthodontic device as claimed in claim 2, wherein the spring member free end portion engages an adjacent surface of the pivot portion of the slot closure member, and said adjacent surface comprises a cam surface so shaped that when the slot closure member is in slot open position it moves the free end portion out of the arch wire receiving slot.

4. An orthodontic device as claimed in claim 1, wherein in slot closed position the slot closure part of the slot closure portion buts against an adjacent surface of the arch wire receiving slot to establish the fully closed position of the slot closure member.

5. An orthodontic device as claimed in claim 4, wherein the slot closure part or the device body has formed therein between the butting surfaces a tool-receiving recess elongated in the mesial-distal direction and opening to the butting surfaces, the tool-receiving recess permitting insertion therein of the flattened end of an opening tool which upon rotation about a labial-lingual axis moves the slot closure member toward the slot open position.

6. An orthodontic device as claimed in claim 1, wherein the pivot and slot closure portions are connected by an intervening arm portion;
   wherein the pivot and arm portions are movable between slot open and slot closed positions in a recess opening centrally to one of the surface portions of the device body; and
   wherein in slot closed position corresponding surfaces of the pivot and arm portions are flush with the device body surface portion in which the recess is formed.

7. An orthodontic device as claimed in claim 1, wherein the pivot and slot closure portions are connected by an intervening arm portion joined to the body engaging part of the slot closure portion at a junction; and
   wherein the junction is of reduced mesial-distal dimension to thereby increase the effective mesial-distal length of the body engaging part available for said flexing.

8. An orthodontic device as claimed in claim 1, wherein the slot closure member is mounted by the device body for movement about the pivot axis by two separate pivot pin sections mounted in the device body with their respective axes inclined either both labially or both lingually, so that they urge the slot closure member respectively labially or lingually into the interference fit butting engagement, whereby movement of the slot closure member into the slot closed position requires flexing of the pivot pin sections as well as of the body engaging part against their elasticity.

9. An orthodontic device as claimed in claim 1, wherein at least one of a surface portion of the body engaging part that in the slot closed position engages the adjacent surface portion of the device body part to provide the retaining force, and said adjacent surface portion of the device body part, is provided with a thin adherent coating to increase the retaining force between them.

10. An orthodontic bracket comprising:
    a bracket body having labial lingual, gingival, occlusal, mesial and distal portions, the body having therein a mesial-distal extending arch wire receiving slot with its labial or lingual side open respectively to the labial or lingual surface portion to permit insertion of an arch-wire into the slot, and
    a slot closure member pivotally mounted by the bracket body so as to be movable about a pivot axis between a slot open position in which the open slot side is open, and a slot closed position in which it closes the open slot side to retain an arch wire in the slot;
    wherein the slot closure member comprises:
       a pivot portion mounted by the bracket body for the pivoting movement of the slot closure member about the pivot axis, and
       a slot closure portion movable with the pivot portion and extending mesially-distally with respect to the bracket body; and
    wherein the slot closure portion comprises:
       a slot closure part that in the slot closes the open side of the arch wire slot; and
       at least one mesially-distally extending body engaging part that in the slot closed position of the slot closure member engages with an adjacent surface portion of the bracket body with an interference fit butting engagement between them providing a retaining force such that the slot closure member is retained thereby in the slot closed position, and such that movement of the slot closure member into the slot closed position requires flexing of the bracket engaging part in a direction away from the bracket body against the elasticity of the material of the body engaging part.

11. An orthodontic bracket as claimed in claim 10, wherein there is provided within the bracket body a flat attitude controlling spring member having a fixed end portion fixed to the bracket body and a free end portion extending into the arch wire receiving slot for engagement in a mesially-distally extending plane with an arch wire in the slot, such engagement urging the arch wire toward the slot closure part.

12. An orthodontic bracket as claimed in claim 11, wherein the free end portion of the spring member engages an adjacent surface of the pivot portion, and said adjacent surface comprises a cam surface so shaped that when the slot closure member is in slot open position it moves the free end portion out of the arch wire receiving slot.

13. An orthodontic bracket as claimed in claim 12, and comprising an auxiliary spring member operative with the cam surface with the slot closure member in slot closed position to assist in retaining the slot closure member in that position.

14. An orthodontic bracket as claimed in claim 11, wherein the fixed end portion of the spring member is sandwiched between the bracket body and a foil member attached to the labial or the lingual surface portion of the bracket body, which foil member is in turn sandwiched between the bracket body and a tooth to which the bracket is to be attached.

15. An orthodontic bracket as claimed in claim 14, wherein the fixed end portion of the spring member is provided with a through aperture and the spring, the bracket body and the foil member are attached to one another by upsetting a portion of the bracket body or the foil member into the through aperture.

16. An orthodontic bracket as claimed in claim 11, wherein the bracket body comprises therein a mesially-distally extending ledge behind which the free end portion of the spring member can be engaged to prevent engagement between the free end portion and an arch wire within the archwire slot.

17. An orthodontic bracket as claimed in claim 10, wherein the bracket body has a recess therein in which the slot closure member moves, the recess opening centrally to the bracket body gingival or occlusal surface portion, and
    wherein in slot closed position respective gingival or occlusal surfaces of the pivot and slot closure portions are flush with the corresponding bracket body surface portion.

18. An orthodontic bracket as claimed in claim 10, and for application to the lingual surface of an incisor or canine tooth, which teeth are characterized in that their labial-lingual dimension increases progressively from the gingival to the occlusal;
    wherein the bracket body has therein a recess opening to the lingual and occlusal surface portions in which the slot closure member is mounted so as to be movable between the slot open and closed positions;
    wherein in the slot closed position the occlusal surface portion of the slot closure member is flush with the occlusal surface portion of the bracket body to thereby provide a combined occlusal surface which is unobstructed; and
    wherein the gingival-occlusal dimension of the bracket body decreases progressively from the lingual to the labial, the decrease corresponding to the average increase from the occlusal to the gingival of an incisor or canine tooth, so that when the bracket is attached to the lingual surface of an incisor or canine tooth the unobstructed combined occlusal surface provides a mesial-distal, labial-lingual extending bite plane surface which the tooth edge at the junction of the occlusal and labial surface portions of an opposed incisor or canine tooth can engage during biting action to oppose overbite.

19. An orthodontic bracket as claimed in claim 10, wherein in slot closed position the slot closure part of the slot closure portion buts against the gingival or occlusal surface of the arch wire receiving slot to establish the fully slot closed position of the slot closure member.

20. An orthodontic bracket as claimed in claim 19, wherein the slot closure part or the bracket body has formed therein between the butting surfaces a tool-receiving recess elongated in the mesial-distal direction and opening to the butting surfaces, the tool-receiving recess permitting insertion therein of the flattened end of an opening tool which upon rotation about a labial-lingual axis moves the slot closure member toward the slot open position.

21. An orthodontic bracket as claimed in claim 10, wherein the pivot and slot closure portions are connected by an intervening arm portion joined to the body engaging part of the slot closure portion at a junction; and
    wherein the junction is of reduced mesial-distal dimension to thereby increase the effective mesial-distal length of the body engaging part available for said flexing.

22. An orthodontic bracket as claimed in claim 10, wherein the slot closure member is mounted by the bracket body for movement about the pivot axis by two separate pivot pin sections mounted in the bracket body with their respective axes inclined either both labially or both lingually, so that they urge the slot closure member respectively labially or lingually into the interference fit butting engagement, whereby movement of the slot closure member into the slot closed position requires flexing of the pivot pin sections as well as of the body engaging part against their elasticity.

23. An orthodontic bracket as claimed in claim 10, wherein the bracket body comprises two mesially-distally spaced pairs of gingivally-occlusally extending tie wings with the slot closure member mounted by the body between the tie wing pairs.

24. An orthodontic bracket as claimed in claim 10, wherein at least one of a surface portion of the body engaging part that in the slot closed position engages the adjacent surface portion of the bracket body part to provide the retaining force, and said adjacent surface portion of the bracket body part, is provided with a thin adherent coating to increase the retaining force between them.

25. An orthodontic convertible buccal tube comprising:
    a buccal tube body having labial, lingual, gingival, occlusal, mesial and distal surface portions, the body having therein a mesial-distal extending arch wire receiving slot having one side open to one of the surface portions to permit insertion of an arch wire into the slot, and
    a slot closure member mounted by the buccal tube body so as to be movable about a pivot axis between a slot open position in which the open slot side is open, and a slot closed position in which the closure member closes the open slot side to retain an arch wire in the slot;
    wherein the slot closure member comprises:
        a pivot portion mounted by the buccal tube body for the pivoting movement of the slot closure member about the pivot axis; and
        a slot closure portion movable with the pivot portion and extending mesially-distally with respect to the device body;

and wherein the slot closure portion comprises:
- a slot closure part that in the slot closed position closes the open side of the arch wire slot; and
- at least one mesially-distally extending body engaging part that in the slot closed position of the slot closure member engages with an adjacent surface portion of the buccal tube body with an interference fit engagement between them such that the slot closure member is retained thereby in the slot closed position, and movement of the slot closure member to and from the slot closed position requires flexing of the body engaging part in a direction away from the buccal tube body against the elasticity of the material of the body engaging part.

26. A convertible buccal tube as claimed in claim 25, wherein there is provided within a recess within the tube body a flat attitude controlling spring member having a fixed end portion fixed to the tube body and a free end portion extending into the arch wire receiving slot for engagement in a mesially-distally extending plane with an arch wire in the slot, such engagement urging the arch wire toward the slot closure part.

27. A convertible buccal tube as claimed in claim 26, wherein the free end portion of the spring member engages an adjacent surface of the pivot portion, and said adjacent surface comprises a cam surface so shaped that when the slot closure member is in slot open position it moves the free end portion out of the arch wire receiving slot.

28. A convertible buccal tube as claimed in claim 27, and comprising an auxiliary spring member operative with the cam surface with the slot closure member in slot closed position to assist in retaining the slot closure member in that position.

29. A convertible buccal tube as claimed in claim 26, wherein the tube body comprises therein a mesially-distally extending ledge behind which the free end portion of the spring member can be engaged to prevent engagement between the free end portion and an arch wire within the archwire slot.

30. A convertible buccal tube as claimed in claim 25, wherein the pivot and slot closure portions are connected by an intervening arm portion;
- the intervening arm portion is movable between slot open and slot closed positions in a recess opening centrally to the occlusal or labial surface portion of the buccal tube body;
- and in slot closed position a corresponding surface of the arm portion is flush respectively with the buccal tube occlusal or labial body surface portion.

31. A convertible buccal tube as claimed in claim 25, wherein in slot closed position the slot closure part of the slot closure portion butts against a corresponding surface of the arch wire receiving slot to establish the fully closed position of the slot closure member.

32. A convertible buccal tube as claimed in claim 31, wherein the slot closure part or the tube body has formed therein between the butting surfaces a tool-receiving recess elongated in the mesial-distal direction and opening to the butting surfaces, the tool-receiving recess permitting insertion therein of the flattened end of an opening tool which upon rotation about a labial-lingual axis moves the slot closure member toward the slot open position.

33. A convertible buccal tube as claimed in claim 25, wherein the pivot and slot closure portions are connected by an intervening arm portion joined to the body engaging part of the slot closure portion at a junction; and
- wherein the junction is of reduced mesial-distal dimension to thereby increase the effective mesial-distal length of the body engaging part available for said flexing.

34. A convertible buccal tube as claimed in claim 25, wherein at least one of a surface portion of the body engaging part that in the slot closed position engages the adjacent surface portion of the buccal tube body part to provide the retaining force, and said adjacent surface portion of the buccal tube body part, is provided with a thin adherent coating to increase the retaining force between them.

35. An orthodontic bracket for application to the lingual surface of an incisor or canine tooth, which teeth are characterized in that their labial-lingual dimension increases progressively from the gingival to the occlusal, the bracket comprising:
- a bracket body having labial, lingual, gingival, occlusal, mesial and distal surface portions, having therein a mesial-distal extending arch wire receiving slot with its lingual side open to the lingual surface portion to permit insertion of an arch wire into the slot, and having therein a recess opening to the lingual and occlusal surface portions;
- the bracket body also comprising a slot closure member mounted by the bracket body in the recess so as to be movable about a pivot axis between a slot open position in which the open slot side is open, and a slot closed position in which it closes the open slot side to retain an orthodontic arch wire therein, the slot closure member also having labial, lingual, gingival, occlusal, mesial and distal surface portions;
- wherein in the slot closed position the occlusal surface portion of the slot closure member is flush with the occlusal surface portion of the bracket body to thereby provide a combined occlusal surface which is unobstructed; and
- wherein the gingival-occlusal dimension of the bracket body decreases progressively from the lingual to the labial, the decrease corresponding to the average increase from the occlusal to the gingival of an incisor or canine tooth, so that when the bracket is attached to the lingual surface of an incisor or canine tooth the unobstructed combined occlusal surface provides a mesial-distal, labial-lingual extending bite plane surface which the tooth edge at the junction of the occlusal and labial surface portions of an opposed incisor or canine tooth can engage during biting action to oppose overbite.

* * * * *